US012672838B2

(12) United States Patent
Fieselmann et al.

(10) Patent No.: US 12,672,838 B2
(45) Date of Patent: Jul. 7, 2026

(54) METHOD FOR A POSITIONING CONTROL OF AN OBJECT UNDER INVESTIGATION BEFORE ACQUIRING A PROJECTIVE X-RAY IMAGE

(71) Applicant: Siemens Healthineers AG, Forchheim (DE)

(72) Inventors: Andreas Fieselmann, Erlangen (DE); Ramyar Biniazan, Nuremberg (DE); Sven-Martin Sutter, Herzogenaurach (DE); Magdalena Herbst, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 18/774,292

(22) Filed: Jul. 16, 2024

(65) Prior Publication Data

US 2025/0025123 A1     Jan. 23, 2025

(30) Foreign Application Priority Data

Jul. 18, 2023    (EP) ..................................... 23186133

(51) Int. Cl.
| | |
|---|---|
| *A61B 6/00* | (2024.01) |
| *A61B 6/04* | (2006.01) |
| *A61B 6/50* | (2024.01) |
| *G06T 7/00* | (2017.01) |
| *G06V 10/25* | (2022.01) |
| *G06V 20/64* | (2022.01) |
| *G06V 40/10* | (2022.01) |

(52) U.S. Cl.
CPC ................ *A61B 6/545* (2013.01); *A61B 6/04* (2013.01); *A61B 6/505* (2013.01); *G06T 7/0012* (2013.01); *G06V 10/25* (2022.01);

*G06V 20/653* (2022.01); *G06V 40/103* (2022.01); *G06T 2207/10116* (2013.01); *G06T 2207/30008* (2013.01)

(58) Field of Classification Search
CPC ........... A61B 6/545; A61B 6/505; A61B 6/04
See application file for complete search history.

(56) References Cited

U.S. PATENT DOCUMENTS

| | | | |
|---|---|---|---|
| 5,001,885 A | 3/1991 | Borella | |
| 2018/0116613 A1 | 5/2018 | Von Berg et al. | |

(Continued)

FOREIGN PATENT DOCUMENTS

| | | |
|---|---|---|
| EP | 0356651 A1 | 3/1990 |

OTHER PUBLICATIONS

Lin S., Lai Yu-kun et al.:"Color-aware surface registration, Computers & Graphics", vol. 58, 2016, pp. 31-42, https://doi.org/10.1016/j.cag.2016.05.007.

*Primary Examiner* — Carolyn A Pehlke
(74) *Attorney, Agent, or Firm* — Harness, Dickey & Pierce, P.L.C.

(57) ABSTRACT

A computer-implemented method for position control of an object under investigation before acquiring a projective X-ray image of a region of interest, the computer-implemented method comprising: receiving object information of the object under investigation in an examination pose; retrieving an object model relating to the examination pose and the region of interest; adapting the object model to the object under investigation based on the object information; and evaluating the examination pose based on the adapted object model.

17 Claims, 3 Drawing Sheets

(56)            References Cited

U.S. PATENT DOCUMENTS

| | | | |
|---|---|---|---|
| 2019/0096520 A1* | 3/2019 | Strobel | G06T 7/149 |
| 2020/0375546 A1 | 12/2020 | Shoudy et al. | |
| 2021/0093284 A1 | 4/2021 | Sutter et al. | |
| 2023/0157660 A1 | 5/2023 | Tu et al. | |
| 2023/0290053 A1* | 9/2023 | Bu | G06T 15/00 |
| 2024/0197274 A1* | 6/2024 | Sato | G06T 7/0012 |
| 2025/0127476 A1* | 4/2025 | Sun | A61B 6/102 |

* cited by examiner

FIG 2

METHOD FOR A POSITIONING CONTROL OF AN OBJECT UNDER INVESTIGATION BEFORE ACQUIRING A PROJECTIVE X-RAY IMAGE

CROSS-REFERENCE TO RELATED APPLICATION(S)

The present application claims priority under 35 U.S.C. § 119 to European Patent Application No. 23186133.7, filed Jul. 18, 2023, the entire contents of which is incorporated herein by reference.

FIELD

One or more example embodiments of the present invention relate to a computer-implemented method for a positioning control of an object under investigation before acquiring a projective X-ray image of a region of interest, a computer-implemented method to create a set of reference object models for at least one examination pose and at least one region of interest, a medical system, a computer program and a non-transitory computer-readable medium, which provide an evaluation of an examination pose before acquiring a projective X-ray image.

BACKGROUND

In X-ray imaging, projective X-ray images are common for many imaging tasks. In a projective X-ray geometry, structures may overlap. X-rays are emitted by an X-ray source, partially absorbed by the tissue and bones of the object under investigation, and, finally, the remainder of the X-rays is registered by the X-ray detector. As output, an X-ray image can be displayed.

Measurements of length and angles are frequently made in musculoskeletal (MSK) X-ray examinations to assess orthopedic diseases. The accuracy of the measurement depends on the quality of the acquired image. Various factors that degrade image quality exist. For example, non-optimal patient positioning, especially relative to the X-ray source and the X-ray detector, can lead to an overlap of structures in the projection image and thereby incorrect measurement values.

Radiographers are well trained to assure best possible patient positioning such that the image can be used for the indication for which it was acquired. Physical disabilities of the patient must be taken into account when finding the most suitable positioning for this individual patient. The level of expertise of radiographers can vary. Therefore, the capability to find the best possible patient position can vary and depend on the radiographer.

Up to now patient positioning is normally assessed by the radiographer. Few automated software solutions exist for dedicated applications (e. g. chest x-ray exam) that provide feedback to the radiographer after the exam has been acquired. So far, no automated solution exists that can assess the patient positioning before the x-rays are released.

SUMMARY

A technical problem to be overcome by one or more embodiments of the present invention is that the image quality, especially with respect to the patient positioning, depends on the expertise of the radiographer acquiring the exam or rather the X-ray image.

It is an object of one or more embodiments of the present invention to provide a method which evaluates the patient positioning before acquiring the X-ray image by technical mechanisms and/or means.

According to one or more embodiments of the present invention, at least the object is achieved by the features of the accompanying claims, in particular of a method, the respective computer program product, the non-transitory computer-readable medium, and system. Advantageous aspects, features and embodiments are described in the claims and in the following description together with advantages.

Independent of the grammatical term usage, individuals with male, female or other gender identities are included within the term.

An embodiment of the present invention relates to a computer-implemented method for a positioning control of an object under investigation before acquiring a projective X-ray image of a region of interest, comprising:

receiving an object information of the object under investigation in an examination pose, retrieving an object model relating to the examination pose and the region of interest, adapting the object model to the object under investigation based on the object information, and evaluating the examination pose based on the adapted object model.

The computer-implemented method, according to an embodiment of the present invention, is used to control or to check a positioning of an object under investigation before acquiring a projective X-ray image of a region of interest. Typically, the object under investigation is a patient.

The method comprises the steps of receiving, retrieving, adapting, and evaluating, preferably in the given order. An object information of the object under investigation in an examination pose is received. An object model relating to the examination pose and the region of interest is retrieved, e.g. from a database. The object model is adapted to the object under investigation based on the object information. The examination pose is evaluated based on the adapted object model.

In order to be able to use this method, at least one object model, preferably a plurality of object models, are made available. The inventors propose to create a number of reference object models based on an avatar-based simulation phase. This step can be required to be done only once per measurement application. Results from this step can be used in the steps of adapting the object model to the object under investigation, the assessment or evaluation based on the matched avatar or adapted object model, and/or a recommendation of alternative positioning based on data of individual patients or individual objects under investigation.

The aim of the avatar-based simulation phase is to explore the relationship between patient positioning as the patient is represented by an avatar or by the object model and its impact on the measurement result. The results of simulation phase provide a relationship between the positioning of the object under investigation, which can be represented by the object model, and the impact on the measurement result, especially based on an acquired X-ray image of the object under investigation which is positioned in that specific position and/or pose.

Preferably, different object models are made available. A specific object model can be selected from the plurality of object models. The plurality of object models can include object models of young, old, normal, obese, slim, small, large or medium sized patients. The object under investigation is preferably a human patient. Anatomical models of the relevant anatomy, e.g. based on CT volumes, can be used to refine the object model. In a preferred embodiment, a motion model for the object model can be required in addition to the anatomical model. The motion model can provide a model regarding realistic motion of bones. The object model includes at least one landmark, especially a plurality of relevant landmarks, in 3D for the corresponding measurement task or examination. In a preferred embodiment, the object model must include relevant landmarks in 3D for the corresponding measurement task or examination. The imaging process is modelled by a forward projector for the landmarks in X-ray geometry. The landmarks of the object model are projected in X-ray geometry into an imaging plane. The anatomical model as well as the motion model are used to modify the object model in order to provide a reference object model wherein the patient position parameters p can be used to characterize the reference object model and/or the object model.

For the measurement task, which could be indicated by index j, but is omitted here in most formulas for better readability, relevant patient position parameters p must be defined. These comprise the patient posture, the patient orientation relative to the imaging setup and the geometry of the imaging system.

A reference position pref needs to be defined: pref=[p1ref, p2ref . . . ] T.

For this reference position, the projected 2D landmarks lref are obtained by applying the forward projection to the 3D landmarks lvol of the object model at position pref. From pref, the reference measurement mref is calculated using the function mref=Mj(pref) where Mj( ) describes the measurement process for a particular measurement or examination. The reference position can characterize the pose and/or the position of the reference object model, especially in a standard examination pose. The position can characterize an examination pose which can be different to the standard examination pose.

Equally, measurements mi for positions pi covering the parameter space are obtained. The deviation di=mref−mi=M (pref)−M(pi)=D(pi)

of the measurements mi to the reference measurement mref can be given as relative or absolute deviation. D( ) is a function depending on pi that computes the deviation for a pre-defined pref. The values di corresponding to pi are stored in a database. The values di can be given as absolute or relative values.

By receiving an object information of the object under investigation in an examination pose, object information is provided e.g. based on information acquired by an external source or sensor, or the X-ray detector in combination with the X-ray source, especially a pre-shot X-ray image acquisition. The object information can be a depth image of the object under investigation. The object information can be determined based on an image of the object under investigation. The object under investigation is positioned preferably according to the examination pose in connection with the X-ray system. A specific examination pose is assigned to a specific X-ray examination. An examination pose can describe e.g. a standing, sitting or lying pose. The examination pose can include instructions for angles or rotations of body parts.

According to an aspect of an embodiment of the present invention, the object information is determined based on an image of the surface of the object under examination. The image of the surface can be acquired by a sensor or an external source. The external source or the sensor that records the external appearance of the patient, especially not recording the interior of the object under investigation, can include:

an RGB camera, a depth camera, a structured light camera, an infrared camera, and/or a light detection and ranging (LiDAR) camera.

The external source or the sensor can be positioned at the medical system, at the imaging device or at a different location in the examination room.

The object information can be determined e.g. based on a landmark detection method. The object information can be determined e.g. based on a detection of the outline of the object under investigation. The object information can comprise a parameter relating to the size and/or weight of the object under investigation. The size can describe the full body length, or a measure of a body part or a body region. The object information can comprise the outer shape of the object under examination, especially the outer shape which can be observed from the position of the X-ray source. The outer shape can be made available in a grid representation comprising the depth information of at least a part of the object under examination.

According to an aspect of an embodiment of the present invention, the object information is determined based on an X-ray image. The X-ray image can be a low dose X-ray pre-shot image. The low dose X-ray pre-shot image can show some information of the interior of the object under investigation but with less detail compared to a full X-ray image. An X-ray pre-shot could be used to acquire an image, in this case, the image comprises information of the internal appearance of body of the object under examination. The X-ray image can show details in a two-dimensional plane like the outline as well as some information about the internal structures of the object under investigation. The internal structures can comprise information about dense objects like bones, about soft tissue and/or about air volumes. The X-ray image provides two-dimensional information displayed by gray values.

By retrieving an object model relating to the examination pose and the region of interest, the object model is selected according to the examination pose and the region of interest and the object model made available to the system.

In a next step, the avatar can be matched to object under investigation. This means that the object model can be adapted to the object under investigation based on the object information. The object model can be called an avatar. The object model can be adapted or modified based on the object information. The object information can comprise parameters like dimensions of anatomical structures or dimensions of the outer shape of the object under investigation.

Data from external sources can be used to adapt the parameters of the avatar to the real patient. The object information can be acquired by external sources like a camera. The object information can comprise parameters which describe at least the outer shape of the object under investigation, respectively the patient. The object information is used to adapt the object model to the object under investigation. Preferably, the object information comprises a set of parameters which describe the object under investigation as well as the object model. A parameter could be for example the width of the chest of the object under investigation and the object model, respectively. The object information is used to adapt the object model in a way that at least the outer shape of the object is represented by the adapted object model.

To match the object model to the object under investigation, one has to find the correct surface transformation between surface of the object model and the object under investigation. Various methods for this task have been proposed in literature and could be used for this task. The work by Shuai Lin, Yu-Kun Lai, Ralph R. Martin, Shiyao Jin, Zhi-Quan Cheng, Color-aware surface registration, Computers & Graphics, Volume 58, 2016, Pages 31-42, https://doi.org/10.1016/j.cag.2016.05.007, for example, introduced a novel color-aware registration method for rigid and non-rigid registration in which the inputs from depth cameras will provide initial alignment and deformable registration steps will improve it for having a surface with high quality textures. It is known that this step has a certain range of accuracy due to individual characteristics of the object under investigation. Nevertheless, one can use this step or this method to obtain a statistical estimation with a certain confidence range.

According to an aspect of an embodiment of the present invention, the object model is adapted by using a surface transformation function based on the object information. The surface or the outer shape of the object model can be adapted to the surface or the outer shape of the object under investigation. The object information can be used to bring the surface of the object model in conformity with the surface of the object under investigation, at least to a certain degree.

Surface transformations of a human shape based on depth images are well known. These transformations involve the analysis and manipulation of depth images to extract meaningful information about the shape and structure of human bodies. By understanding the surface properties of a human shape, a gesture recognition and a pose estimation can be performed based on (depth) images.

Depth images capture the distance information of objects in a scene, typically represented as a two-dimensional matrix of depth values. These depth values provide a measurement of the distance between the camera and the observed object's surface. For human bodies, depth images can offer valuable insights into the shape, posture, and movements of individuals, as they can capture the three-dimensional geometry of the human form.

Surface transformations in this context can involve various techniques to process and analyze depth images to extract useful features or parameters. One of the fundamental tasks is the extraction of the human body's skeletal structure or pose estimation. This process involves detecting key joints, such as the head, shoulders, elbows, wrists, hips, knees, and ankles, and estimating their positions in three-dimensional space.

Another important surface transformation is shape analysis, which aims to extract shape descriptors and characteristics from depth images. Shape analysis techniques can provide insights into body proportions, body segment lengths, and even detect anomalies or deviations from normal body structures. The information gathered by the surface transformation can comprise parameters describing the object under investigation based on the object information, e.g. a depth image.

According to an aspect of an embodiment of the present invention, the surface transformation function is a rigid registration function or a non-rigid registration function.

Rigid transformations refer to transformations that preserve the shape and size of an object. These transformations include translation, rotation, and reflection. The transformation involves moving an object or shape without changing its orientation or size. It is characterized by shifting the object's position in a specific direction. The rotation involves rotating an object or shape around a fixed point, often referred to as the center of rotation. The object maintains its size and shape but is repositioned at a different angle. The reflection is a transformation that involves flipping or mirroring an object or shape across a line or plane. The object appears as a mirror image of itself but retains its shape and size.

Non-rigid transformations, also known as deformations, refer to transformations that can change the shape and size of an object. Unlike rigid transformations, non-rigid transformations can alter the local geometry of an object. These transformations are used to model objects that can undergo elastic deformations, such as the human body. Non-rigid transformations can comprise scaling, shearing, bending or warping.

The scaling is a non-rigid transformation that involves resizing an object or shape. It can either increase or decrease the size of an object uniformly or along different dimensions. The shearing is a non-rigid transformation that skews the shape of an object along one or more axes. It distorts the object by displacing points in a particular direction proportional to their distance from a reference line. Bending or warping involves nonlinear deformations that change the shape of an object in a localized manner. These transformations are used to model complex deformations in objects or surfaces.

In a next step, the examination pose is evaluated based on the adapted object model. The assessment of the positioning can be determined based on the matched avatar or the adapted object model. In this step, the results from the avatar-based simulation phase and adapting the object model to the object under investigation based on the object information can be combined. The object model parameters of the adapted object model are used as input for querying the database created by the avatar-based simulation phase and the statistical most likely measurement deviation is obtained. In case the measurement deviation exceeds a pre-defined threshold, the human operator can be informed about the deviation.

According to an aspect of an embodiment of the present invention, the object model further relates to the object information. The object information can comprise a parameter like age, height, weight or other descriptive parameters of the object under investigation. The corresponding object model can be described by the same parameter with at least a similar value.

According to an aspect of an embodiment of the present invention, the adapted object model is defined by object model parameters. The object model parameters can comprise a set of parameters describing the object model. The object model parameters can be used for the determination of the deviation. By querying the database based on the object model parameters, a deviation can be estimated or determined.

According to an aspect of an embodiment of the present invention, a reference object model is selected based on the object model parameters from a plurality of reference object models with assigned positioning deviations compared to a standard examination pose. The reference object models can be stored in a database. Due to the finite nature of a database, the object model parameters can be used to select a reference object model out of a plurality of reference object models. A reference object model can be selected based on a comparison of object model parameters describing the adapted object model with corresponding parameters of the reference object models.

According to an aspect of an embodiment of the present invention, an output is generated, if the positioning deviation of the selected reference object model exceeds a predefined threshold. The user can receive a message, if the positioning deviation exceeds a predefined threshold. An exceeded predefined threshold can correspond to malpositioning or a bad positioning of the object under investigation which would lead to a bad image for the imaging task or examination. The output can be displayed on a display. The output can be communicated to the user via optic, acoustic or haptic mechanisms, devices and/or means. The amount of deviation can be made available to the user. Therefore, the user can decide whether a change of the position or pose of the object under investigation is needed or possible, especially regarding individual circumstances or individual parameters.

According to an aspect of an embodiment of the present invention, the output is a proposal for an improved examination pose which is determined based on an individual parameter of the object under investigation. According to an aspect of an embodiment of the present invention, the individual parameter comprises individual restrictions of mobility or individual restrictions due to pain associated with an examination pose. The individual parameter can describe an amount of pain, e.g. related to a movement of a joint or a fixation of a joint, e.g. by a plaster cast.

In a preferred embodiment, a recommendation of an alternative positioning is proposed to the user. When patient positioning has been evaluated to be suboptimal, especially a statistical measurement deviation exceeds a certain threshold, then a more suitable positioning of the object under investigation can be suggested by the system. This suggestion or this proposal can also include individual restrictions of the patient, e. g. due to physical disabilities.

Mathematically, the new suggested patient positioning can be described by the avatar parameters: psugg=[p1sugg, p2sugg, ... ] T.

p1sugg could refer to a specific flexion of the knee and p2sugg could refer to a specific internal rotation of the knee, for example. The following relation must be fulfilled for a suggested new patient positioning:

$$D(psugg) \leq tD$$

where D( ) is the measurement deviation depending on avatar parameters (see the step of adapting the object model to the object under investigation based on the object information) and tD is a threshold value.

For individual patients, some patient positions may not be easily possible or may be painful, e.g. due to physical disabilities. Cpat(p) is a function that describes the cost associated with a certain patient positioning for a certain patient (how it can be determined is described below). The cost is very high for positions that are not easily possible since they are painful.

The task is to find psugg such that $$D(psugg) \leq tD \text{ and } Cpat(psugg) \leq tC$$

where tC is the maximum tolerable cost. The task can be reformulated to minimize the following function $$f(psugg) = D(psugg) - b * Cpat(psugg)$$

with chosen weighting b between measurement deviation and cost.

Standard methods for this optimization task exist. The function Cpat(p) has to be determined individually for each patient. Thus, individual information about the patient is necessary to construct this function. The individual information could be obtained by using room camera that record the mobility of the patient, for example. Other sources from which Cpat(p) can be determined are previous images or patient records. If patient-individual information is not available a statistical average from a population could be selected.

To sum up, one or more embodiments of the present invention solve at least the problem using in a preferred embodiment the following steps:

Step 0: Avatar-based simulation phase which can provide a set of reference object models as output;

Step 1: Match avatar to patient which can comprise the steps of receiving an object information of the object under investigation in an examination pose, retrieving an object model relating to the examination pose and the region of interest, and adapting the object model to the object under investigation based on the object information, Step 2: Assessment based on matched avatar which can comprise evaluating the examination pose based on the adapted object model, Step 3 (optional): Recommendation of alternative positioning which can comprise a proposal for an improved ex-amination pose which is determined based on an individual parameter of the object under investigation.

Compared to a visual assessment by the radiographer or user which is current standard of care, one or more embodiments of the present invention provide an automated assessment that is less subjective and more time efficient. As a unique feature, the painfulness of the patient positioning for certain patients is included in the determination of a more optimal patient positioning. The patient positioning can be assessed before X-ray radiation has been delivered to the patient which is an advantage and helps to work according to the ALARA principle to reduce the dose for the patient as much as possible. In case a pre-shot image is involved, only a low amount of X-ray radiation dose would be needed in order to assess the quality of the positioning.

One or more embodiments of the present invention further relate to a computer-implemented method to create a set of reference object models for at least one examination pose and at least one region of interest, comprising:

providing a plurality of different object models comprising at least one landmark for the corresponding region of interest, adapting the plurality of different object models to the at least one examination pose to generate reference object models, for each reference object model, generating a forward projection of the at least one landmark comprised by the reference object model in an X-ray geometry relating to the examination pose and the region of interest, providing the plurality of different object models in a standard examination pose, generating a forward projection of the at least one landmark comprised by the object model in a standard examination pose in the X-ray geometry relating to the examination pose and the region of interest, and determining a positioning deviation by comparing the forward projection of the reference object model to a forward projection of the corresponding object model in the standard examination pose.

A set of reference object models is created for at least one examination pose and at least one region of interest. The region of interest can be specified by an imaging task. The region of interest usually relates to a anatomical region of the object under investigation, e.g. thorax, shoulder or any other part of the human body.

A plurality of different object models comprising at least one landmark for the corresponding region of interest is provided. The plurality of different object models can be stored in a database. The plurality of different object models can be retrieved from the database.

The plurality of different object models is adapted to the at least one examination pose to generate reference object models. The at least one examination pose can deviate from a standard examination pose. A plurality of examination poses can provide a variety of deviations from a standard examination pose wherein the deviation can range from minor deviations to strong deviations.

For each reference object model, a forward projection of the at least one landmark comprised by the reference object model is generated in an X-ray geometry relating to the examination pose and the region of interest.

In addition, the plurality of different object models is provided in a standard examination pose. A forward projection of the at least one landmark comprised by the object model is generated in a standard examination pose in the X-ray geometry relating to the examination pose and the region of interest.

A positioning deviation is determined by comparing the forward projection of the reference object model to the forward projection of the corresponding object model in the standard examination pose.

In order to be able to use this method, at least one object model, preferably a plurality of object models, are made available. The inventors propose to create a number of reference object models based on an avatar-based simulation phase. This step can be required to be done only once per measurement application. Results from this step can be used in the steps of adapting the object model to the object under investigation, the assessment or evaluation based on the matched avatar or adapted object model, and/or a recommendation of alternative positioning based on data of individual patients or individual objects under investigation.

The aim of the avatar-based simulation phase is to explore the relationship between patient positioning as the patient is represented by an avatar or by the object model and its impact on the measurement result. The results of simulation phase provide a relationship between the positioning of the object under investigation, which can be represented by the object model, and the impact on the measurement result, especially based on an acquired X-ray image of the object under investigation which is positioned in that specific position and/or pose.

Preferably, different object models are made available. A specific object model can be selected from the plurality of object models. The plurality of object models can include object models of young, old, normal, obese, slim, small, large or medium sized patients. The object under investigation is preferably a human patient. Anatomical models of the relevant anatomy, e.g. based on CT volumes, can be used to refine the object model. In a preferred embodiment, a motion model for the object model can be required in addition to the anatomical model. The motion model can provide a model regarding realistic motion of bones. The object model includes at least one landmark, especially a plurality of relevant landmarks, in 3D for the corresponding measurement task or examination. In a preferred embodiment, the object model must include relevant landmarks in 3D for the corresponding measurement task or examination. The imaging process is modelled by a forward projector for the landmarks in X-ray geometry. The landmarks of the object model are projected in X-ray geometry into an imaging plane. The anatomical model as well as the motion model are used to modify the object model in order to provide a reference object model wherein the patient position parameters p can be used to characterize the reference object model and/or the object model.

For the measurement task, which could be indicated by index j, but is omitted here in most formulas for better readability, relevant patient position parameters p must be defined. These comprise the patient posture, the patient orientation relative to the imaging setup and the geometry of the imaging system.

A reference position pref needs to be defined: $pref=[p1ref, p2ref \ldots ] T$.

For this reference position, the projected 2D landmarks lref are obtained by applying the forward projection to the 3D landmarks lvol of the object model at position pref. From pref, the reference measurement mref is calculated using the function $mref=Mj(pref)$ where $Mj(\ )$ describes the measurement process for a particular measurement or examination. The reference position can characterize the pose and/or the position of the reference object model, especially in a standard examination pose. The position can characterize an examination pose which can be different to the standard examination pose.

Equally, measurements mi for positions pi covering the parameter space are obtained. The deviation $$di = mref - mi = M(pref) - M(pi) = D(pi)$$

of the measurements mi to the reference measurement mref can be given as relative or absolute deviation. $D(\ )$ is a function depending on pi that computes the deviation for a pre-defined pref. The values di corresponding to pi are stored in a database. The values di can be given as absolute or relative values.

One or more embodiments of the present invention further relate to a medical X-ray system comprising: a first interface, configured for receiving object information of the object under investigation in an examination pose, a second interface, configured for retrieving an object model relating to the examination pose and a region of interest, a third interface, configured for adapting the object model to the object under investigation based on the object information, a fourth interface, configured for evaluating the examination pose based on the adapted object model.

One or more embodiments of the present invention further relate to a computer program product comprising instructions which, when the program is executed by a computer, cause the computer to carry out the method according to One or more embodiments of the present invention.

One or more embodiments of the present invention further relate to a non-transitory computer-readable medium comprising instructions which, when executed by a computer, cause the computer to carry out the method according to one or more embodiments of the present invention.

BRIEF DESCRIPTION OF THE DRAWINGS

Examples of embodiments of the present invention are explained in more detail below with regard to the drawings.

FIG. 2 is a schematic representation of the method to create a set of reference object models for at least one examination pose and at least one region of interest, according to one or more embodiments of the present invention.

DETAILED DESCRIPTION

Figure 1:
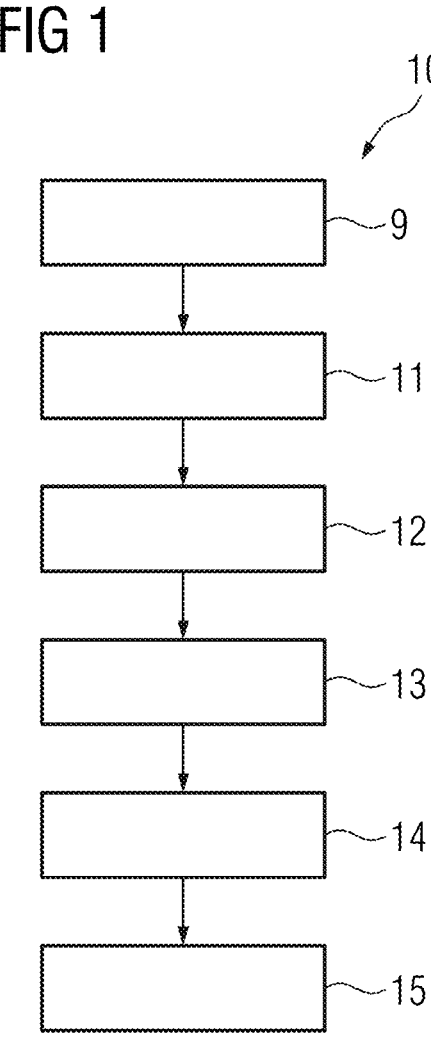
FIG. 1 is a schematic representation of the method for a positioning control of an object under investigation before acquiring a projective X-ray image of a region of interest, according to one or more embodiments of the present invention.

FIG. 1 shows an exemplary embodiment of a computer-implemented method 10 according to one or more embodiments of the present invention. It is a method 10 for a positioning control of an object under investigation before acquiring a projective X-ray image of a region of interest, comprising:

receiving 11 an object information of the object under investigation in an examination pose, retrieving 12 an object model relating to the examination pose and the region of interest, adapting 13 the object model to the object under investigation based on the object information, evaluating 14 the examination pose based on the adapted object model.

The computer-implemented method 10, according to one or more embodiments of the present invention, is used to control or to check a positioning of an object under investigation before acquiring a projective X-ray image of a region of interest. Typically, the object under investigation is a human patient.

The method 10 comprises the steps of receiving 11, retrieving 12, adapting 13, and evaluating 14, preferably in the given order. An object information of the object under investigation in an examination pose is received. An object model relating to the examination pose and the region of interest is retrieved, e.g. from a database. The object model is adapted to the object under investigation based on the object information. The examination pose is evaluated based on the adapted object model.

In order to be able to use this method 10, at least one object model, preferably a plurality of object models, are made available. The inventors propose to create a number of reference object models based on an avatar-based simulation phase. This step can be required to be done only once per measurement application. Results from this step can be used in the steps of adapting the object model to the object under investigation, the assessment or evaluation based on the matched avatar or adapted object model, and/or a recommendation of alternative positioning based on data of individual patients or individual objects under investigation.

The aim of the avatar-based simulation phase is to explore the relationship between patient positioning as the patient is represented by an avatar or by the object model and its impact on the measurement result. The results of simulation phase provide a relationship between the positioning of the object under investigation, which can be represented by the object model, and the impact on the measurement result, especially based on an acquired X-ray image of the object under investigation which is positioned in that specific position and/or pose.

Preferably, different object models are made available. A specific object model can be selected from the plurality of object models. The plurality of object models can include object models of young, old, normal, obese, slim, small, large or medium sized patients. The object under investigation is preferably a human patient. Anatomical models of the relevant anatomy, e.g. based on CT volumes, can be used to refine the object model. In a preferred embodiment, a motion model for the object model can be required in addition to the anatomical model. The motion model can provide a model regarding realistic motion of bones. The object model includes at least one landmark, especially a plurality of relevant landmarks, in 3D for the corresponding measurement task or examination. In a preferred embodiment, the object model must include relevant landmarks in 3D for the corresponding measurement task or examination. The imaging process is modelled by a forward projector for the landmarks in X-ray geometry. The landmarks of the object model are projected in X-ray geometry into an imaging plane. The anatomical model as well as the motion model are used to modify the object model in order to provide a reference object model wherein the patient position parameters p can be used to characterize the reference object model and/or the object model.

For the measurement task, which could be indicated by index j, but is omitted here in most formulas for better readability, relevant patient position parameters p must be defined. These comprise the patient posture, the patient orientation relative to the imaging setup and the geometry of the imaging system.

A reference position pref needs to be defined: pref=[p1ref, p2ref . . . ] T.

For this reference position, the projected 2D landmarks lref are obtained by applying the forward projection to the 3D landmarks lvol of the object model at position pref. From pref, the reference measurement mref is calculated using the function mref=Mj(pref) where Mj( ) describes the measurement process for a particular measurement or examination. The reference position can characterize the pose and/or the position of the reference object model, especially in a standard examination pose. The position can characterize an examination pose which can be different to the standard examination pose.

Equally, measurements mi for positions pi covering the parameter space are obtained. The deviation $$di = mref - mi = M(pref) - M(pi) = D(pi)$$

of the measurements mi to the reference measurement mref can be given as relative or absolute deviation. D( ) is a function depending on pi that computes the deviation for a pre-defined pref. The values di corresponding to pi are stored in a database. The values di can be given as absolute or relative values.

By receiving 11 an object information of the object under investigation in an examination pose, object information is provided e.g. based on information acquired by an external source or sensor, or the X-ray detector in combination with the X-ray source, especially a pre-shot X-ray image acquisition. The object information can be a depth image of the object under investigation. The object information can be determined based on an image of the object under investigation. The object under investigation is positioned preferably according to the examination pose in connection with the X-ray system. A specific examination pose is assigned to a specific X-ray examination. An examination pose can describe e.g. a standing, sitting or lying pose. The examination pose can include instructions for angles or rotations of body parts.

In a preferred embodiment, the object information is determined based on an image of the surface of the object under examination. The image of the surface can be acquired by a sensor or an external source. The external source or the sensor that records the external appearance of the patient, especially not recording the interior of the object under investigation, can include:

an RGB camera, a depth camera, a structured light camera, an infrared camera, and/or a light detection and ranging (LiDAR) camera.

The external source or the sensor can be positioned at the medical system, at the imaging device or at a different location in the examination room.

The object information can be determined e.g. based on a landmark detection method. The object information can be determined e.g. based on a detection of the outline of the object under investigation. The object information can comprise a parameter relating to the size and/or weight of the object under investigation. The size can describe the full body length, or a measure of a body part or a body region. The object information can comprise the outer shape of the object under examination, especially the outer shape which can be observed from the position of the X-ray source. The outer shape can be made available in a grid representation comprising the depth information of at least a part of the object under examination.

In another embodiment, the object information is determined based on an X-ray image. The X-ray image can be a low dose X-ray pre-shot image. The low dose X-ray pre-shot image can show some information of the interior of the object under investigation but with less detail compared to a full X-ray image. An X-ray pre-shot could be used to acquire an image, in this case, the image comprises information of the internal appearance of body of the object under examination. The X-ray image can show details in a two-dimensional plane like the outline as well as some information about the internal structures of the object under investigation. The internal structures can comprise information about dense objects like bones, about soft tissue and/or about air volumes. The X-ray image provides two-dimensional information displayed by gray values.

By retrieving 12 an object model relating to the examination pose and the region of interest, the object model is selected according to the examination pose and the region of interest and the object model made available to the system.

In a next step, the avatar can be matched to object under investigation. This means that the object model can be adapted to the object under investigation based on the object information. The object model can be called an avatar. The object model can be adapted or modified based on the object information. The object information can comprise parameters like dimensions of anatomical structures or dimensions of the outer shape of the object under investigation.

Data from external sources can be used to adapt the parameters of the avatar to the real patient. The object information can be acquired by external sources like a camera. The object information can comprise parameters which describe at least the outer shape of the object under investigation, respectively the patient. The object information is used to adapt the object model to the object under investigation. Preferably, the object information comprises a set of parameters which describe the object under investigation as well as the object model. A parameter could be for example the width of the chest of the object under investigation and the object model, respectively. The object information is used to adapt the object model in a way that at least the outer shape of the object is represented by the adapted object model.

To match the object model to the object under investigation, one has to find the correct surface transformation between surface of the object model and the object under investigation. Various methods for this task have been proposed in literature and could be used for this task. The work by Shuai Lin, Yu-Kun Lai, Ralph R. Martin, Shiyao Jin, Zhi-Quan Cheng, Color-aware surface registration, Computers & Graphics, Volume 58, 2016, Pages 31-42, https://doi.org/10.1016/j.cag.2016.05.007, for example, introduced a novel color-aware registration method for rigid and non-rigid registration in which the inputs from depth cameras will provide initial alignment and deformable registration steps will improve it for having a surface with high quality textures. It is known that this step has a certain range of accuracy due to individual characteristics of the object under investigation. Nevertheless, one can use this step or this method to obtain a statistical estimation with a certain confidence range.

In a preferred embodiment, the object model is adapted by using a surface transformation function based on the object information. The surface or the outer shape of the object model can be adapted to the surface or the outer shape of the object under investigation. The object information can be used to bring the surface of the object model in conformity with the surface of the object under investigation, at least to a certain degree.

Surface transformations of a human shape based on depth images are well known. These transformations involve the analysis and manipulation of depth images to extract meaningful information about the shape and structure of human bodies. By understanding the surface properties of a human shape, a gesture recognition and a pose estimation can be performed based on (depth) images.

Depth images capture the distance information of objects in a scene, typically represented as a two-dimensional matrix of depth values. These depth values provide a measurement of the distance between the camera and the observed object's surface. For human bodies, depth images can offer valuable insights into the shape, posture, and movements of individuals, as they can capture the three-dimensional geometry of the human form.

Surface transformations in this context can involve various techniques to process and analyze depth images to extract useful features or parameters. One of the fundamental tasks is the extraction of the human body's skeletal structure or pose estimation. This process involves detecting key joints, such as the head, shoulders, elbows, wrists, hips, knees, and ankles, and estimating their positions in three-dimensional space.

Another important surface transformation is shape analysis, which aims to extract shape descriptors and characteristics from depth images. Shape analysis techniques can provide insights into body proportions, body segment lengths, and even detect anomalies or deviations from normal body structures. The information gathered by the surface transformation can comprise parameters describing the object under investigation based on the object information, e.g. a depth image.

In a preferred embodiment, the surface transformation function is a rigid registration function or a non-rigid registration function.

Rigid transformations refer to transformations that preserve the shape and size of an object. These transformations include translation, rotation, and reflection. The transformation involves moving an object or shape without changing its orientation or size. It is characterized by shifting the object's position in a specific direction. The rotation involves rotating an object or shape around a fixed point, often referred to as the center of rotation. The object maintains its size and shape but is repositioned at a different angle. The reflection is a transformation that involves flipping or mirroring an object or shape across a line or plane. The object appears as a mirror image of itself but retains its shape and size.

Non-rigid transformations, also known as deformations, refer to transformations that can change the shape and size of an object. Unlike rigid transformations, non-rigid transformations can alter the local geometry of an object. These transformations are used to model objects that can undergo elastic deformations, such as the human body. Non-rigid transformations can comprise scaling, shearing, bending or warping.

The scaling is a non-rigid transformation that involves resizing an object or shape. It can either increase or decrease the size of an object uniformly or along different dimensions. The shearing is a non-rigid transformation that skews the shape of an object along one or more axes. It distorts the object by displacing points in a particular direction proportional to their distance from a reference line. Bending or warping involves nonlinear deformations that change the shape of an object in a localized manner. These transformations are used to model complex deformations in objects or surfaces.

In a next step, the examination pose is evaluated based on the adapted object model. The assessment of the positioning can be determined based on the matched avatar or the adapted object model. In this step, the results from the avatar-based simulation phase and adapting the object model to the object under investigation based on the object information can be combined. The object model parameters of the adapted object model are used as input for querying the database created by the avatar-based simulation phase and the statistical most likely measurement deviation is obtained. In case the measurement deviation exceeds a pre-defined threshold, the human operator can be informed about the deviation.

In a preferred embodiment, the object model further relates to the object information. The object information can comprise a parameter like age, height, weight or other descriptive parameters of the object under investigation. The corresponding object model can be described by the same parameter with at least a similar value.

In a preferred embodiment, the adapted object model is defined by object model parameters. The object model parameters can comprise a set of parameters describing the object model. The object model parameters can be used for the determination of the deviation. By querying the database based on the object model parameters, a deviation can be estimated or determined.

In a preferred embodiment, a reference object model is selected based on the object model parameters from a plurality of reference object models with assigned positioning deviations compared to a standard examination pose. The reference object models can be stored in a database. Due to the finite nature of a database, the object model parameters can be used to select a reference object model out of a plurality of reference object models. A reference object model can be selected based on a comparison of object model parameters describing the adapted object model with corresponding parameters of the reference object models.

In a preferred embodiment, an output is generated, if the positioning deviation of the selected reference object model exceeds a predefined threshold. The user can receive a message, if the positioning deviation exceeds a predefined threshold. An exceeded predefined threshold can correspond to malpositioning or a bad positioning of the object under investigation which would lead to a bad image for the imaging task or examination. The output can be displayed on a display. The output can be communicated to the user via optic, acoustic or haptic mechanisms, devices and/or means. The amount of deviation can be made available to the user. Therefore, the user can decide whether a change of the position or pose of the object under investigation is needed or possible, especially regarding individual circumstances or individual parameters.

According to an aspect of one or more embodiments of the present invention, the output is a proposal 15 for an improved examination pose which is determined based on an individual parameter of the object under investigation. According to an aspect of one or more embodiments of the present invention, the individual parameter comprises individual restrictions of mobility or individual restrictions due to pain associated with an examination pose. The individual parameter can describe an amount of pain, e.g. related to a movement of a joint or a fixation of a joint, e.g. by a plaster cast.

In a preferred embodiment, a recommendation of an alternative positioning is proposed to the user. When patient positioning has been evaluated to be suboptimal, especially a statistical measurement deviation exceeds a certain threshold, then a more suitable positioning of the object under investigation can be suggested by the system. This suggestion or this proposal can also include individual restrictions of the patient, e. g. due to physical disabilities.

Mathematically, the new suggested patient positioning can be described by the avatar parameters:
psugg=[p1sugg, p2sugg, . . . ] T.
p1sugg could refer to a specific flexion of the knee and p2sugg could refer to a specific internal rotation of the knee, for example. The following relation must be fulfilled for a suggested new patient positioning:

$$D(psugg) \leq tD$$

where D( ) is the measurement deviation depending on avatar parameters (see the step of adapting the object model to the object under investigation based on the object information) and tD is a threshold value.

For individual patients, some patient positions may not be easily possible or may be painful, e.g. due to physical disabilities. Cpat(p) is a function that describes the cost associated with a certain patient positioning for a certain patient (how it can be determined is described below). The cost is very high for positions that are not easily possible since they are painful.

The task is to find psugg such that $$D(psugg) \leq tD \text{ and } Cpat(psugg) \leq tC$$

where tC is the maximum tolerable cost. The task can be reformulated to minimize the following function $$f(psugg) = D(psugg) - b * Cpat(psugg)$$

with chosen weighting b between measurement deviation and cost.

Standard methods for this optimization task exist. The function Cpat(p) has to be determined individually for each patient. Thus, individual information about the patient is necessary to construct this function. The individual information could be obtained by using room camera that record the mobility of the patient, for example. Other sources from which Cpat(p) can be determined are previous images or patient records. If patient-individual information is not available a statistical average from a population could be selected.

In step 9, the object information is determined based on an image of the surface of the object under examination. The object information can be represented by a depth or X-ray image of the object under investigation. The object information can be determined based on an X-ray image.

In step 13, the object model is adapted by using a surface transformation function based on the object information. The surface transformation function is a rigid registration function or a non-rigid registration function.

In step 12, the object model further relates to the object information, e.g. age or height. In step 13, the adapted object model is defined by object model parameters.

In step 14, a reference object model is selected based on the object model parameters from a plurality of reference object models with assigned positioning deviations compared to a standard examination pose. The object model can be stored in a database.

An output is generated, if the positioning deviation of the selected reference object model exceeds a predefined threshold.

In step 15, an output is generated and the output is a proposal for an improved examination pose which is determined based on individual parameters of the object under investigation. Individual parameters can comprise a parameter regarding pain. The individual parameters comprise individual restrictions of mobility or individual restrictions due to pain associated with an examination pose.

Figure 2:
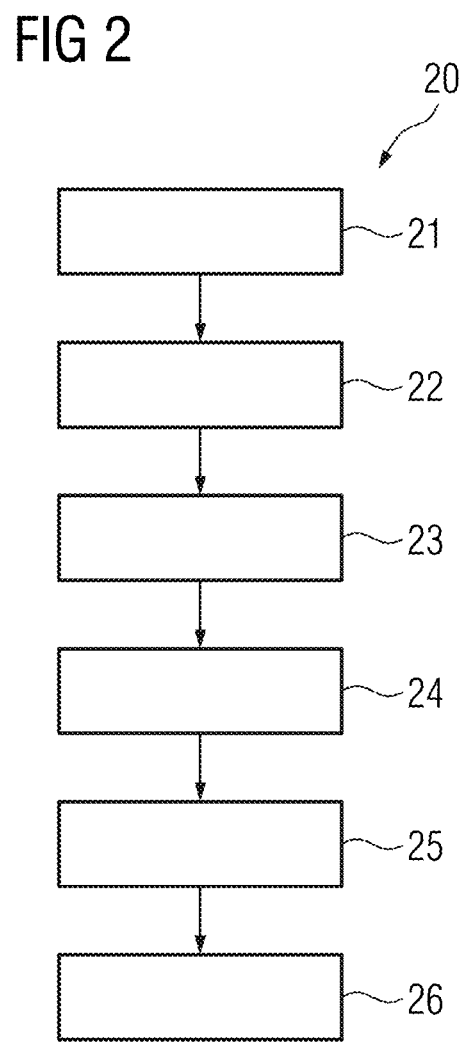

FIG. 2 shows an exemplary embodiment of a computer-implemented method 20 to create a set of reference object models for at least one examination pose and at least one region of interest, comprising:

providing 21 a plurality of different object models comprising at least one landmark for the corresponding region of interest, adapting 22 the plurality of different object models to the at least one examination pose to generate reference object models, for each reference object model, generating 23 a forward projection of the at least one landmark comprised by the reference object model in an X-ray geometry relating to the examination pose and the region of interest, providing 24 the plurality of different object models in a standard examination pose, generating 25 a forward projection of the at least one landmark comprised by the object model in a standard examination pose in the X-ray geometry relating to the examination pose and the region of interest, and determining 26 a positioning deviation by comparing the forward projection of the reference object model to a forward projection of the corresponding object model in the standard examination pose.

A set of reference object models is created for at least one examination pose and at least one region of interest. The region of interest can be specified by an imaging task. The region of interest usually relates to a anatomical region of the object under investigation, e.g. thorax, shoulder or any other part of the human body.

A plurality of different object models comprising at least one landmark for the corresponding region of interest is provided in step 21. The plurality of different object models can be stored in a database. The plurality of different object models can be retrieved from the database.

In step 22, the plurality of different object models is adapted to the at least one examination pose to generate reference object models. The at least one examination pose can deviate from a standard examination pose. A plurality of examination poses can provide a variety of deviations from a standard examination pose wherein the deviation can range from minor deviations to strong deviations.

For each reference object model, a forward projection of the at least one landmark comprised by the reference object model is generated in an X-ray geometry relating to the examination pose and the region of interest in step 23.

In addition, the plurality of different object models is provided in a standard examination pose in step 24. A forward projection of the at least one landmark comprised by the object model is generated in a standard examination pose in the X-ray geometry relating to the examination pose and the region of interest in step 25.

In step 26, a positioning deviation is determined by comparing the forward projection of the reference object model to the forward projection of the corresponding object model in the standard examination pose.

In order to be able to use the method for a positioning control of an object under investigation before acquiring a projective X-ray image of a region of interest, at least one object model, preferably a plurality of object models, are made available. The inventors propose to create a number of reference object models based on an avatar-based simulation phase. This step can be required to be done only once per measurement application. Results from this step can be used in the steps of adapting the object model to the object under investigation, the assessment or evaluation based on the matched avatar or adapted object model, and/or a recommendation of alternative positioning based on data of individual patients or individual objects under investigation.

The aim of the avatar-based simulation phase is to explore the relationship between patient positioning as the patient is represented by an avatar or by the object model and its impact on the measurement result. The results of simulation phase provide a relationship between the positioning of the object under investigation, which can be represented by the object model, and the impact on the measurement result, especially based on an acquired X-ray image of the object under investigation which is positioned in that specific position and/or pose.

Preferably, different object models are made available. A specific object model can be selected from the plurality of object models. The plurality of object models can include object models of young, old, normal, obese, slim, small, large or medium sized patients. The object under investigation is preferably a human patient. Anatomical models of the relevant anatomy, e.g. based on CT volumes, can be used to refine the object model. In a preferred embodiment, a motion model for the object model can be required in addition to the anatomical model. The motion model can provide a model regarding realistic motion of bones. The object model includes at least one landmark, especially a plurality of relevant landmarks, in 3D for the corresponding measurement task or examination. In a preferred embodiment, the object model must include relevant landmarks in 3D for the corresponding measurement task or examination. The imaging process is modelled by a forward projector for the landmarks in X-ray geometry. The landmarks of the object model are projected in X-ray geometry into an imaging plane. The anatomical model as well as the motion model are used to modify the object model in order to provide a reference object model wherein the patient position parameters p can be used to characterize the reference object model and/or the object model.

For the measurement task, which could be indicated by index j, but is omitted here in most formulas for better readability, relevant patient position parameters p must be defined. These comprise the patient posture, the patient orientation relative to the imaging setup and the geometry of the imaging system.

A reference position pref needs to be defined: pref=[p1ref, p2ref . . . ] T.

For this reference position, the projected 2D landmarks lref are obtained by applying the forward projection to the 3D landmarks lvol of the object model at position pref. From pref, the reference measurement mref is calculated using the function mref=Mj(pref) where Mj( ) describes the measurement process for a particular measurement or examination. The reference position can characterize the pose and/or the position of the reference object model, especially in a standard examination pose. The position can characterize an examination pose which can be different to the standard examination pose.

Equally, measurements mi for positions pi covering the parameter space are obtained. The deviation $$di = mref - mi = M(pref) - M(pi) = D(pi)$$

of the measurements mi to the reference measurement mref can be given as relative or absolute deviation. D( ) is a function depending on pi that computes the deviation for a pre-defined pref. The values di corresponding to pi are stored in a database. The values di can be given as absolute or relative values.

Figure 3:
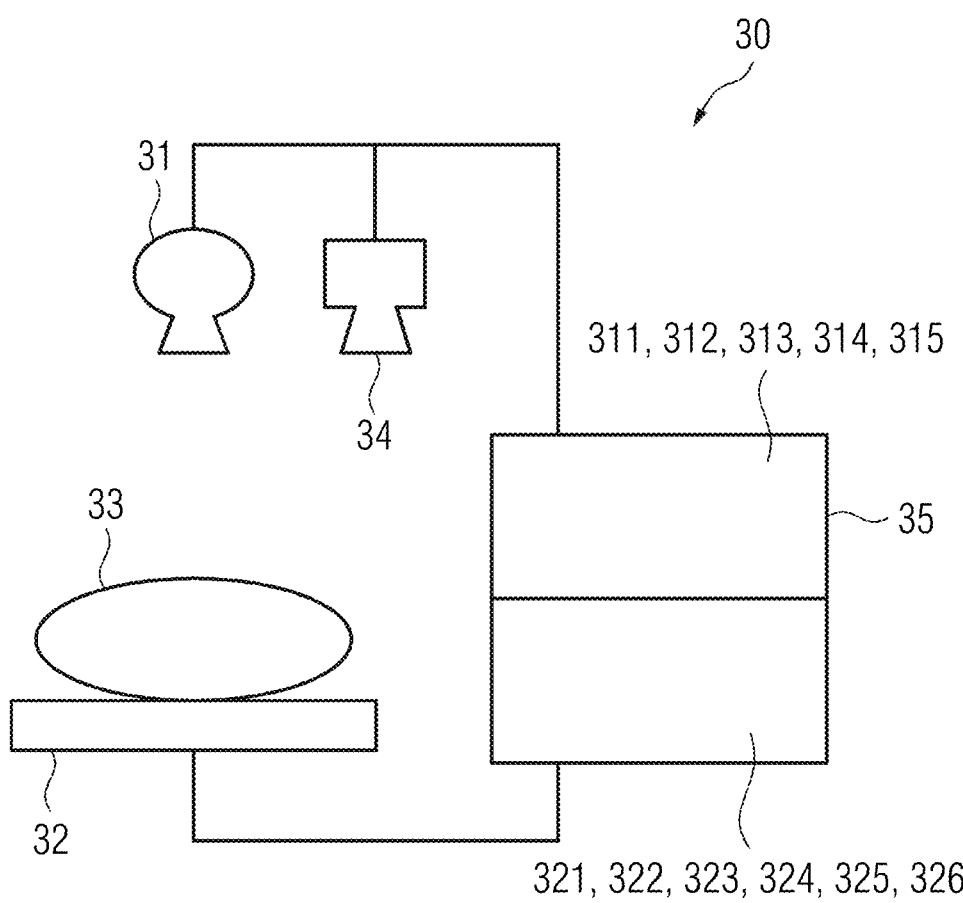
FIG. 3 is a schematic representation of the medical system according to one or more embodiments of the present invention.

FIG. 3 shows an exemplary embodiment of a medical X-ray system comprising:

a first interface 311, configured for receiving object information of the object under investigation in an examination pose, a second interface 312, configured for retrieving an object model relating to the examination pose and a region of interest, a third interface 313, configured for adapting the object model to the object under investigation based on the object information, a fourth interface 314, configured for evaluating the examination pose based on the adapted object model.

The interfaces 311 to 314 can be comprised by a computation unit 35. The computation unit 35 can further comprise units regarding the computer-implemented method to create a set of reference object models for at least one examination pose and at least one region of interest, comprising:

a providing unit 321, configured for providing a plurality of different object models comprising at least one landmark for the corresponding region of interest, an adapting unit 322, configured for adapting the plurality of different object models to the at least one examination pose to generate reference object models, a generating unit 323, configured for generating a forward projection of the at least one landmark comprised by the reference object model in an X-ray geometry relating to the examination pose and the region of interest for each reference object model, a providing unit 324, configured for providing the plurality of different object models in a standard examination pose, a generating unit, configured for generating a forward projection of the at least one landmark comprised by the object model in a standard examination pose in the X-ray geometry relating to the examination pose and the region of interest, and a determining unit 326, configured for determining a positioning deviation by comparing the forward projection of the reference object model to a forward projection of the corresponding object model in the standard examination pose.

In an alternative embodiment, the units 321 to 326 are comprised by a separate computation unit.

In a preferred embodiment, the X-ray system 30 is a radiography system. In an alternative embodiment, the X-ray system 30 can be an angiography system, a fluoroscopy system, a mammography system, or a computed tomography system. The X-ray system 30 comprises an X-ray source 31 which emits X-rays towards the object under investigation 33. At least some of the X-rays can be registered by the X-ray detector 32. In a preferred embodiment, the external sensor is a (depth) camera 34. The camera 34, the X-ray source 31 and the X-ray detector 32 are connected to the computation unit 35.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been further illustrated in detail by the preferred embodiments, the present invention is not limited by the disclosed examples and other variations may be derived therefrom by those skilled in the art without departing from the scope of protection of the present invention.

What is claimed is:

1. A computer-implemented method for position control of an object under investigation before acquiring a projective X-ray image of a region of interest, the computer-implemented method comprising:

receiving object information for the object under investigation in an examination pose;

retrieving an object model relating to the examination pose and the region of interest;

adapting the object model to the object under investigation based on the object information; and evaluating the examination pose based on the adapted object model, wherein

27 the adapted object model is defined by object model parameters, and based on the object model parameters, a reference object model is selected from a plurality of reference object models with assigned positioning deviations relative to a standard examination pose for a respective examination type for the region of interest.

2. The computer-implemented method according to claim 1, wherein the object information is determined based on an image of a surface of the object under investigation.

3. The computer-implemented method according to claim 1, wherein the object information is determined based on an X-ray image.

4. The computer-implemented method according to claim 1, wherein the object model is adapted using a surface transformation function based on the object information.

5. The computer-implemented method according to claim 4, wherein surface transformation function is a rigid registration function or a non-rigid registration function.

6. The computer-implemented method according to claim 1, wherein the object model further relates to at least one descriptive parameter of the object information.

7. The computer-implemented method according to claim 1, further comprising:

generating an output in response to the assigned positioning deviation of the reference object model exceeding a threshold.

8. The computer-implemented method according to claim 7, wherein the output is a proposal for an improved examination pose which is determined based on an individual parameter of the object under investigation.

9. The computer-implemented method according to claim 8, wherein the individual parameter includes individual restrictions of mobility or individual restrictions due to pain associated with an examination pose.

10. The computer-implemented method according to claim 2, wherein the object information is determined based on an X-ray image.

11. The computer-implemented method according to claim 10, wherein the object model is adapted using a surface transformation function based on the object information.

12. The computer-implemented method of claim 1, wherein the standard examination pose is an ideal standard examination pose.

13. A method to create a set of reference object models for at least one examination pose and at least one region of interest, the set of reference object models configured for inclusion in the computer-implemented method of claim 1, the method comprising:

providing a plurality of different object models including at least one landmark for a corresponding region of interest;

adapting the plurality of different object models to the at least one examination pose to generate reference object models;

generating, for each reference object model, a forward projection of the at least one landmark comprised by the reference object model in an X-ray geometry relating to the examination pose and the region of interest;

providing the plurality of different object models in a standard examination pose;

generating a forward projection of the at least one landmark comprised by an object model in the standard examination pose in the X-ray geometry relating to the examination pose and the region of interest; and determining a positioning deviation by comparing the forward projection of the reference object model to a forward projection of a corresponding object model in the standard examination pose.

14. A medical X-ray system comprising:

a first interface configured to receive object information of an object under investigation in an examination pose;

a second interface configured to retrieve an object model relating to the examination pose and a region of interest;

a third interface configured to adapt the object model to the object under investigation based on the object information; and a fourth interface configured to evaluate the examination pose based on the adapted object model, wherein the adapted object model is defined by object model parameters, and based on the object model parameters, a reference object model is selected from a plurality of reference object models with assigned positioning deviations relative to a standard examination pose for a respective examination type for the region of interest.

15. A non-transitory computer-readable medium storing a computer program product comprising instructions that, when executed by a computer, cause the computer to carry out the computer-implemented method of claim 2.

16. A non-transitory computer-readable medium comprising instructions that, when executed by a computer, cause the computer to carry out the computer-implemented method of claim 1.

17. A medical X-ray system comprising:

a memory storing computer executable instructions; and at least one processor configured to execute the computer executable instructions to cause the medical X-ray system to receive object information of an object under investigation in an examination pose, retrieve an object model relating to the examination pose and a region of interest, adapt the object model to the object under investigation based on the object information, and evaluate the examination pose based on the adapted object model, wherein the adapted object model is defined by object model parameters, and based on the object model parameters, a reference object model is selected from a plurality of reference object models with assigned positioning deviations relative to a standard examination pose for a respective examination type for the region of interest.

* * * * *